United States Patent [19]

Peel et al.

[11] 4,326,034

[45] Apr. 20, 1982

[54] FERMENTATION PROCESS FOR PRODUCING HIGHER PLANT CELLS

[75] Inventors: Eric Peel, Shepperton; Colin C. Dalton, Laleham, both of England

[73] Assignee: The British Petroleum Company Limited, London, England

[21] Appl. No.: 65,002

[22] Filed: Aug. 8, 1979

[30] Foreign Application Priority Data

Aug. 16, 1978 [GB] United Kingdom ............... 33470/78

[51] Int. Cl.$^3$ .............................................. C12N 5/02
[52] U.S. Cl. ...................................... 435/241; 435/818
[58] Field of Search ................................ 435/240, 241

[56] References Cited

U.S. PATENT DOCUMENTS 3,816,960  6/1974  Gudin et al. .

OTHER PUBLICATIONS

American Journal of Botany, vol. 50, pp. 248–254 (1963).

*Primary Examiner*—Alvin E. Tanenholtz
*Attorney, Agent, or Firm*—Morgan, Finnegan, Pine, Foley and Lee

[57] ABSTRACT

Higher plant cells (e.g. cells of Spermatophyta) capable of growing in the presence of light and in the absence of a carbohydrate carbon source are produced from higher plant cells which require a carbohydrate source by cultivation in an aqueous medium in the presence of light, $O_2$ and $CO_2$. The quantity of carbohydrate is reduced during the cultivation while the concentration of dissolved oxygen is maintained at a value below 250 n mol of $O_2$ per ml of medium.

Preferably cultivation is in continuous culture and the preferred dissolved $O_2$ concentration is from 25 to 85 n mol per ml. The $CO_2$ present and the quantum flux density may be increased as the carbohydrate is reduced.

8 Claims, No Drawings

FERMENTATION PROCESS FOR PRODUCING HIGHER PLANT CELLS

The present invention relates to a method for the production of higher plant cells for use in submerged and/or surface fermentation processes in which plant cells are cultivated in the presence of light. More particularly the invention relates to a method for the production of higher plant cells having photosynthetic activity which are capable of growth in the presence of light in or on simple nutrient media consisting essentially of inorganic elements required for growth in the absence of a carbohydrate carbon source. The media can contain small quantities of organic compounds other than carbohydrates such as vitamins and amino acids. By the term higher plant cells is meant, throughout this specification, the cells of any higher plants other than the algae.

Fermentation processes for the surface and submerged culture of cells of higher plants using simple nutrient media which consist essentially of inorganic elements required for growth in the presence or absence of a carbohydrate carbon source are known, for example, from an article by A. C. Hilderbrant, J. C. Wilmar, H. Johns and A. J. Riker in the American Journal of Botany 1963, Vol. 50, pages 248–54. A method for producing modified strains of of higher plant tissues which can be grown in the presence of light on a simple nutrient medium enriched with sugar as a carbon source is described by the present applicants in their British Pat. No. 1,401,681.

The method for producing higher plant cells which are capable of growth in the presence of light and the absence of a carbohydrate carbon source according to the present invention comprises cultivating a higher plant cell which requires a carbohydrate carbon source for growth, in the presence of light, a gas containing free oxygen and a gas containing carbon dioxide, in an aqueous medium consisting essentially of inorganic elements required by the cell for growth and the carbohydrate and maintaining the concentration of dissolved oxygen in the medium at a value below 250 n mol of oxygen per ml of medium whilst reducing the quantity of readily assimilable carbohydrate which is available to the cell to an amount which induces in the cell the development of an enhanced capacity for photosynthesis and continuing cultivation until cells which can grow in the presence of light and in the absence of carbohydrate are produced.

Aqueous nutrient media consisting essentially of inorganic elements which are required by higher plant cells for growth are known and any of these media are suitable for use in the present method. Some examples of media of this type are Skoog, Heller, Knop; Murashige and Skoog; Gamborg and White and Street media. Typically the inorganic elements present in this type of medium include nitrogen, phosphorus, potassium, sodium, calcium, magnesium, iron, zinc, manganese, copper, nickel, cobalt, boron, molybdenum, sulphur, chlorine and iodine. The media are usually made up as aqueous solutions of salts of the elements. Media of this type can and usually do contain small quantities of organic compounds such as amino acids, vitamins, e.g. nicotinic acid, thiamine and folic acid, auxins, cytokinins and other growth factors.

The carbohydrate varies with the species to which the plant cell belongs. The carbohydrate can be readily assimilable by the cell or it can be non-assimilable as such but can be broken down, for example by enzymic action, to form a readily assimilable carbohydrate. The enzyme can be produced by the cell or it can be added separately to the medium. By the term readily assimilable carbohydrate is meant throughout this specification a carbohydrate which can be taken up by the cell without cleavage of the molecule. Some examples of readily assimilable carbohydrates are glucose and fructose. Examples of carbohydrates which are not assimilable but can be utilised by the cell after cleavage of the molecules to form carbohydrates of lower molecular weight which can be assimilated are polysaccharides such as inulin and starch. Some carbohydrates, e.g. maltose, sucrose and lactose can be either readily assimilable or non-assimilable depending on the type of cell and/or the growth conditions.

Suitable carbohydrates for asparagus cells are lactose, sucrose, glucose and starch. Lactose is particularly suitable. Suitable carbohydrates for spinach cells are sucrose, glucose, fructose, inulin, xylose, raffinose, maltose and lactose. Fructose is particularly suitable.

When the carbohydrate is readily assimilable the quantity which is available to the cell can be reduced by limiting the rate at which the carbohydrate is supplied to the cell or the quantity of the carbohydrate added to the medium. On the other hand when the carbohydrate is nonassimilable but can be cleaved by the enzyme system of the cell into assimilable carbohydrate the quantity of the latter which is available to the cell is in most cases governed by the activity of the enzyme system of the cell. Alternatively the enzyme required to cleave the carbohydrate can be added to the medium and the quantity of assimilable carbohydrate released by its action can be controlled by controlling the activity of the enzyme present in the medium.

It is not essential to the operation of the present method to determine the quantity of readily assimilable carbohydrate required to induce the cell to develop an enhanced photosynthetic capacity. For example, when the carbohydrate added to the medium is readily assimilable the method can be operated by gradually reducing the carbohydrate concentration until a cell which is capable of growth in the absence of a carbohydrate is produced. This reduction in the carbohydrate concentration can be effected by gradually diluting the medium in which the cells are cultivated with carbohydrate-free medium. Alternatively the method can be carried out in two stages, in which the quantity of carbohydrate in the second stage is less than that in the first stage. Cultivation in either or both stages can be batch or continuous. In batch culture cells from the first stage can be transferred to a medium in which the quantity of carbohydrate in the second stage is less than that in the first stage. In continuous culture steady state operation can be established in the first stage, the carbohydrate concentration in the medium feed reduced and a new steady state established in the second stage. It is also possible in continuous operation to reduce the quantity of assimilable carbohydrate available to the cell by changing the type of carbohydrate supplied from a readily assimilable carbohydrate to a carbohydrate of the type which can be cleaved by enzymic action preferably that of the cell to an assimilable carbohydrate. The quantity of available assimilable carbohydrate being governed by the activity of enzyme present.

Most suitably the gas containing free oxygen and the gas containing free carbon dioxide can be air and the concentration of dissolved oxygen in the medium can be maintained at a value below 250 n mol per ml of medium by supplying a mixture of air and a biologically inert gas, e.g. nitrogen, to the medium. However, pure oxygen and carbon dioxide can be used. It is desirable to maintain a high gas flow rate in the medium to flush out undesirable volatile compounds, e.g. ethylene, which may be formed by the growing cells and to agitate the cell suspension. This can achieved by mixing the gas containing oxygen and the gas containing carbon dioxide with a substantial volume of a biologically inert gas. Most suitably the minimum value for the dissolved oxygen concentration is about 10 n mol per ml of medium. Preferably the dissolved oxygen concentration can be maintained at a value in the range 25 to 85 n mol per ml of medium. We have found that for spinach cells a preferred value is about 50 n mol of oxygen per ml of medium.

The capacity of the cells to utilise carbon dioxide increases as their capacity for photosynthesis increases. Consequently the quantity of carbon dioxide supplied to the cells can and preferably should be increased as cultivation progresses. This can be done by increasing the amount of carbon dioxide present in the total volume of gas supplied to the medium to a value in the range 0.3 to 2.0 percent by volume and preferably to about 1.0 percent by volume.

Most suitably the light spectrum applied to the cells during cultivation can be in the range 380 n m to 740 n m. The light can be daylight or provided by an artificial source. Artificial light can be supplied by such lamps as white fluorescent tubes or daylight fluorescent tubes either alone or in combination with Grolux fluorescent tubes. Most suitably sufficient light should be applied to the cells to permit chlorophyll synthesis and the development of photosynthetic capacity without causing damage that results in the cells browning. In the initial stages of cultivation quantum flux densities in the range 76 to 200$\mu$ einstein m$^{-2}$s$^{-1}$ are suitable. Most suitably the light energy applied to the cell should be sufficient to allow the photosynthesis rate to exceed the respiration rate. The amount of light required depends on such factors as the cell or biomass concentration and the depth of the culture. In the later stages of cultivation as the photosythetic capacity increases quantum flux densities in the range 100 to 400$\mu$ einstein m$^{-2}$s$^{-1}$ are suitable.

Most suitably sufficient agitation should be applied during cultivation to keep the cells in suspension, reduce the formation of aggregates and to facilitate mixing of the cells, medium and gas. The agitation can be effected by an agitator, e.g. a turbine, paddle or screw or by the gas supplied to the medium as in an air lift fermentation either alone or in combination.

The temperature of the medium during cultivation can be in the range 5° C. to 40° C. depending on the type of cell present. Most suitably the temperature can be in the range 20° C. to 30° C. and preferably in the range 24° C. to 27° C. A temperature of 25° C. is preferred for spinach cells and 26° C. for asparagus cells.

The pH of the medium during cultivation can have a value in the range 3.6 to 7.0 and preferably in the range 4.5 to 5.5.

Cultivation can be carried out under either batch or continuous conditions of operation. Continuous operation is preferable since it permits more control over the environment of the cell. Axenic conditions are preferable since micro-organisms such as fungi and bacteria can outgrow the higher plant cells on the nutrient media used, thus depriving the cells of essential nutrients. Preferably the method can be carried out in vessels made of glass or other readily sterilisable transparent materials.

The present method is applicable to cells of any higher plant which require a carbohydrate as a carbon source for growth. Plant cells from the division Spermatophyta are particularly suitable. Some examples of preferred genera are Spinacia and Asparagus. Examples of preferred species are Spinacia oleracea L. and Asparagus officinalis L. Suspensions of cells or cells in the form of soft callus are most suitable as starting material for the present method. The cells are preferably green in color, i.e. possessing at least some chlorophyll but the presence of chlorophyll is not essential.

By application of the present method to cells of higher plants, cells having a high photosynthetic capacity can be produced. The cells can be fully photoautotrophic when cultivated either on surface or in submerged culture and in consequence they are particularly suitable for use in processes for the production of plant biomass. The biomass can be used as a feedstuff, a source of chemicals or a biotransformation/bioassay system. For example, fully photoautotrophic cells of Spinacia oleracea can be produced which are suitable for use in processes for the production of biomass using simple inorganic media only. Cells of *Asparagus officinalis* can be produced which require certain vitamins, amino acids and other organic growth factors but which do not require an added carbohydrate for growth on simple inorganic media.

The method of the present invention is illustrated further by the following examples.

EXAMPLE 1

400 ml of a suspension containing dispersed undiffenertiated green pigmented cells of spinach (*Spinacia oleracea* L.) which contain chlorophyll but which are dependent on added carbohydrate for growth in the presence of light were inoculated under aseptic conditions into 1500 ml of a heat sterilised aqueous nutrient medium contained in a 2000 ml glass fermentation vessel. The medium consisting essentially of inorganic elements required by the cell for growth had the following composition.

TABLE 1

| Component | Concentration mg. l.$^{-1}$ in Distilled Water |
|---|---|
| NH$_4$NO$_3$ | 825 |
| KNO$_3$ | 950 |
| CaCl$_2$ . 2H$_2$O | 220 |
| MgSO$_4$ . 7H$_2$O | 185 |
| KH$_2$PO$_4$ | 85 |
| Na$_2$-EDTA . 2H$_2$O | 3.7 |
| FeCl$_3$ . 6H$_2$O | 2.7 |
| H$_3$BO$_3$ | 3.1 |
| MnSO$_4$ . 4H$_2$O | 11.15 |
| ZnSO$_4$ . 7H$_2$O | 4.3 |
| KI | 0.415 |
| Na$_2$MoO$_4$ . 2H$_2$O | 0.125 |
| CuSO$_4$ . 5H$_2$O | 0.0125 |
| CoCl$_2$ . 6H$_2$O | 0.0125 |
| Sucrose | 10,000 |
| Glycine | 0.2 |
| Nicotinic acid | 0.05 |
| Pyrodoxin . HCl | 0.05 |
| Thiamin HCl | 0.1 |
| Myo-inositol | 100 |
| Glutamine | 200 |

TABLE 1-continued

| Component | Concentration mg. $1.^{-1}$ in Distilled Water |
|---|---|
| Initial pH | 5.52 |
| Autoclaved at 121° C. | for 20 minutes |
| Volume Autoclaved | 1.5 liters |

The vessel had a working volume of 1700 ml and was aerated by a pipe sparger capable of supplying gas at a rate of 17.65 volume/volume/hour. Four Phillips fluorescent tubes each capable of delivering 65 to 80 watts continuous white light were located at a distance of 14 cm from the wall of the vessel. The lights provided the surface of each vessel with quanta at a rate of $4.28\pm0.6\mu$ einstein sec$^{-1}$ measured in the range 390 to 720 n m.

After inoculation as described above batch operation was commenced and continued for 10.8 days. A mixture of air and nitrogen in a proportion varying with the period of batch culture was supplied to the medium at a rate of 17.65 volume/volume/hour. After 10.8 days of batch fermentation fresh aqueous nutrient medium having the composition described below was fed to the vessel at a dilution rate of $4.2\times10^{-3}$ volume/volume/hour.

TABLE 2

| Component | Concentration mg. $1.^{-1}$ in Distilled Water |
|---|---|
| $NH_4NO_3$ | — |
| $KNO_3$ | 2,956 |
| $CaCl_2 . 2H_2O$ | 220 |
| $MgSO_4 . 7H_2O$ | 185 |
| $KH_2PO_4$ | 85 |
| $Na_2$-EDTA . $2H_2O$ | 3.7 |
| $FeCl_3 . 6H_2O$ | 2.7 |
| $H_3BO_3$ | 3.1 |
| $MnSO_4 . 4H_2O$ | 11.15 |
| $ZnSO_4 . 7H_2O$ | 4.3 |
| KI | 0.415 |
| $Na_2MoO_4 . 2H_2O$ | 0.125 |
| $CuSO_4 . 5H_2O$ | 0.0125 |
| $CoCl_2 . 6H_2O$ | 0.0125 |
| Fructose | 10,000 |
| Glycine | 0.2 |
| Nicotinic acid | 0.05 |
| Pyrodoxin HCl | 0.05 |
| Thiamin HCl | 0.1 |
| Myo-inositol | 100 |
| Glutamine | 200 |
| Initial pH | 4.0 |
| Autoclaved at 121° C. | for 20 minutes |
| Volume Autoclaved | 10 liters |

Steady state conditions were established after 43 days of continuous culture. During this period the cells had negligble photosynthetic capacity and possessed only a small amount of chloroplast pigments. The temperature of the medium throughout this period of batch and continuous culture was 25° C. and the concentration of dissolved oxygen was $74\pm10$ n mol per ml of the medium. These were heterotrophic conditions.

The fructose concentration in the imput medium was then reduced by 50 percent and the partial pressure of the air fed to the vessel was reduced in a step-wise fashion to 39 percent of the original value by dilution with nitrogen. The concentration of dissolved oxygen remained at $74\pm10$ n mol per ml of medium. Steady state conditions of continuous operation were re-established at the same dilution rate ($4.2\times10^{-3}$ v/v/h) and cultivation was continued for 54 days. These were photo-heterotrophic conditions. The cells present in the medium during this period of continuous culture under reduced sugar supply contained more chloroplast pigments and had a greater photosynthetic capacity than those present in the first steady state period of continuous cultivation as can be seen from Table 3. A suspension of cells from the 54 day fermentation was used as a starter culture for a second fermentation vessel which was identical in design to that of the first vessel. The aqueous nutrient medium in the second stage had the composition described above in relation to the continuous culture with the exception that the fructose and the organic growth factors except the chelating agent EDTA were omitted. The quantum flux density applied to the second vessel was increased by 160 percent by the provision of reflectors and by moving the light source closer to the vessel wall. The quantity of carbon dioxide fed to the vessel was increased by approximately 3000 percent. The fermenter was operated at a dilution rate of $2.5\times10^{-3}$ volume/volume/hour.

The second fermentation was then operated without any major changes in the conditions for 86 days. The fermentation temperature was maintained at 25° C. and the pH varied in the range 4.8 to 5.9 but was usually about 5.0. The stirring speed was $36\pm6$ rpm and the fermenter volume varied between 1.8 and 2.0 l. The fermenter was run as a repeated fed batch culture. The volume of 1.8 l was used to calculate dilution rates. The conditions were photoautotrophic and during this period of cultivation the cells were fully photosynthetic, as can be seen from Table 3, and grew satisfactorily in the absence of added sugar and organic growth factors with the exception of EDTA. The biomass dry weight concentration was $3.82\pm0.11$ mg ml$^{-1}$ and the chlorophyll $\alpha+\beta$ concentration was $1397\pm81$ $\mu$g g$^{-1}$ dry weight. The productivity was 0.23 g of freeze dried biomass $1^{-1}$ day$^{-1}$.

Table 3 compares potential photosynthesis of the biomass which was measured using a Clark type oxygen electrode at saturating carbon dioxide and quantum flux density. Potential photosynthesis is expressed in three different ways in each of the three conditions described above.

TABLE 3

| potential photosynthesis rate | heterotrophic conditions | photo-hetereotrophic conditions | photo-autotrophic conditions |
|---|---|---|---|
| n mol $O_2$ . mg$^{-1}$ dry wt. min$^{-1}$ | 0.44 | 7.93 | 9.20 |
| n mol $O_2$ . $10^{-6}$ cells . min$^{-1}$ | 0.88 | 7.31 | — |
| $\mu$ mol $O_2$ . mg$^{-1}$ chlorophyll . h$^{-1}$ | 145 | 425 | 410 |

EXAMPLE 2

360 ml of a suspension culture containing dispersed undifferentiated green pigmented cells of asparagus (Asparagus officinalis L.) which contained chlorophyll but which were dependent on added carbohydrate for growth were inoculated under aseptic conditions into 2.2 liters of a heat sterilised modified Murashige and Skoog aqueous inorganic medium contained in a four liter capacity glass fermentation vessel of the type described by Wilson et al. J Experimental Botany 1971, 22 (70) 197–207. The medium had the composition detailed in Table 4.

TABLE 4

| Component | Concentration mg. $l^{-1}$ in Distilled Water |
|---|---|
| $NH_4NO_3$ | 1650.0 |
| $KNO_3$ | 1900.0 |
| $H_3BO_3$ | 6.2 |
| $KH_2PO_4$ | 170.0 |
| KI | 0.83 |
| $Na_2MoO_4 \cdot 2H_2O$ | 0.25 |
| $CoCl_2 \cdot 6H_2O$ | 0.025 |
| $CaCl_2 \cdot 2H_2O$ | 440.0 |
| $MgSO_4 \cdot 7H_2O$ | 370.0 |
| $MnSO_4 \cdot 4H_2O$ | 22.3 |
| $ZnSO_4 \cdot 7H_2O$ | 8.6 |
| $CuSO_4 \cdot 5H_2O$ | 0.025 |
| $Na_2 \cdot EDTA\ 2H_2O$ | 37.35 |
| $FeSO_4 \cdot 7H_2O$ | 27.85 |
| Thiamine HCl | 0.10 |
| Nicotinic acid | 0.05 |
| Pyridoxine HCl | 0.05 |
| Glycine | 0.20 |
| Biotin | 0.05 |
| Glutamine | 200.00 |
| Myo-inositol | 100.00 |
| Kinetin | 0.1 |
| α naphthalene acetic acid | 1.0 |
| Lactose | 20,000 |
| pH before autoclaving | 6.2 |

The vessel had a working volume of 2.5 liters. The aeration device was a number 2 porosity sinter glass filter. Light was supplied by two banks of equal numbers of 12 inch white and Grolux fluorescent tubes which were capable of giving a quantum flux density of $100\mu$ einstein $m^{-2} s^{-1}$ at the wall of the vessel. The vessel was equipped with a magnetic stirrer.

After inoculation with the cell suspension as described above batch operation was commenced. Light was applied to the vessel for alternating periods of 16 hours light and 8 hour dark. A mixture of air and nitrogen in a proportion of 50 percent by volume of air and 50 percent by volume of nitrogen was supplied to the vessel at a rate of 9.6 volume/volume/hour to give an initial dissolved oxygen concentration in the medium of 100 n mol $ml^{-1}$. The medium was maintained at a temperature of 26° C. Sufficient agitation was applied by the magnetic stirrer to keep the cells in suspension. The fermentation was operated under batch conditions for 11 days during which time the dissolved oxygen concentration fell to 50 n mol $ml^{-1}$. 50 ml samples of the cell suspension thus formed were taken aseptically and inoculated into a series of algal growth tubes each of which contained 200 ml of a carbohydrate-free modified Murashige and Skoog medium, the composition of which is given in Table 5 below. A description of similar growth tubes is given by Bergmann L. in "Les Culture de Tissus de Plantes" Coll CNRE (Strasbourg 1967) 1968 pages 312–221). Each tube had a working volume of 250 ml. The tubes were located in a transparent water bath. Light was applied to the tubes by two banks of equal numbers of 12 inch white and Grolux fluorescent tubes which were capable of giving a mean quantum flux density of $100\mu$ einstein $m^{-2} s^{-1}$ at the wall of each tube. Each tube was aerated by a centrally located pipe sparger. The modified Murashige and Skoog medium had the composition detailed in Table 5.

TABLE 5

| Component | Concentration mg. $l^{-1}$ in Distilled Water |
|---|---|
| $KNO_3$ | 1900.0 |
| $H_3BO_3$ | 6.2 |
| $KH_2PO_4$ | 170.0 |
| KI | 0.83 |
| $Na_2MoO_4 \cdot 2H_2O$ | 0.25 |
| $CoCl_2 \cdot 6H_2O$ | 0.025 |
| $CaCl_2 \cdot 2H_2O$ | 440.0 |
| $MgSO_4 \cdot 7H_2O$ | 370.0 |
| $MnSO_4 \cdot 4H_2O$ | 22.3 |
| $ZnSO_4 \cdot 7H_2O$ | 8.6 |
| $CuSO_4 \cdot 5H_2O$ | 0.025 |
| $Na\text{-}EDTA \cdot 2H_2O$ | 37.35 |
| $FeSO_4 \cdot 7H_2O$ | 27.85 |
| Thiamine HCl | 0.10 |
| Nicotinic acid | 0.05 |
| Pyridoxine HCl | 0.05 |
| Glycine | 0.20 |
| Biotin | 0.05 |
| Glutamine | 200.00 |
| Myo inositol | 100.00 |
| Kinetin | 0.1 |
| α naphthalene acetic acid | 1.0 |
| pH before autoclaving | 4.66 |

Autoclaved at 121° C. for 20 minutes.

The water bath was held at a temperature in the range 24° to 26° C. A mixture of equal volumes air and nitrogen enriched with 2 percent carbon dioxide was supplied to each tube at a gas flow rate of 20 volume/volume/hour. The concentration of dissolved oxygen in the medium was below 125 n mol per ml. Cultivation was continued for a period of three weeks after which the cells were harvested. Samples of the cells were used to inoculate further algal growth tubes of the same type as that described above. Each tube contained 200 ml of the sterilised medium described above with reference to the algal tubes and cultivation was continued for a period of up to two years in the absence of added carbohydrate.

We claim:

1. A method for producing higher plant cells which are capable of growth in the presence of light and the absence of a carbohydrate carbon source comprising cultivating higher plant cells which require a carbohydrate carbon source for growth, in the presence of light, a gas containing free oxygen and a gas containing carbon dioxide, in a liquid aqueous medium consisting essentially of inorganic elements required by the cells for growth and the carbohydrate and maintaining said plant cells in suspension and maintains the concentration of dissolved oxygen in the medium at a value within the range 10 to 250 n mol of oxygen per ml of medium while reducing the quantity of readily assimilable carbohydrate which is available to the cell to an amount which induces in the cell the development of an enhanced capacity for photosynthesis and continuing cultivation until cells which can grow in the presence of light and in the absence of carbohydrate are produced.

2. A method as claimed in claim 1 wherein the concentration of dissolved oxygen is from 25 to 85 n mol per ml.

3. A method as claimed in claim 1 wherein the highe plant cells are cultivated in continuous culture.

4. A method as claimed in claim 1 wherein the quantity of carbon dioxide supplied to the cells is increased as cultivation progresses.

5. A method as claimed in claim 1 wherein the light spectrum applied to the cells is in the range 380 n m to 740 n m.

6. A method as claimed in claim 5 wherein, initially, the quantum flux density is in the range 76 to 200μ einstein $m^{-2}s^{-1}$ and is increased during cultivation to a quantum flux density in the range 100 to 400μ einstein $m^{-2}s^{-1}$.

7. A method as claimed in claim 1 wherein the medium has a temperature of from 5° to 40° C. and a pH of from 3.6 to 7.0.

8. A method as claimed in claim 1 wherein the higher plant cells are from the division Spermatophyta.

* * * * *

UNITED STATES PATENT AND TRADEMARK OFFICE
CERTIFICATE OF CORRECTION

PATENT NO. : 4,326,034

DATED : April 20, 1982

INVENTOR(S) : Eric Peel and Colin C. Dalton

It is certified that error appears in the above—identified patent and that said Letters Patent is hereby corrected as shown below:

In claim 1, line 10, change "maintains" to --maintaining--.

Signed and Sealed this

Seventeenth Day of August 1982

[SEAL]

Attest:

Attesting Officer

GERALD J. MOSSINGHOFF

Commissioner of Patents and Trademarks